(12) United States Patent
He et al.

(10) Patent No.: US 8,710,210 B2
(45) Date of Patent: Apr. 29, 2014

(54) METHOD OF USING N-THIO COMPOUNDS FOR OLIGONUCLEOTIDE SYNTHESIS

(75) Inventors: Yigang He, Ewing, NJ (US); Victor Sorokin, Cincinnati, OH (US); Wieslaw Adam Mazur, Mason, OH (US)

(73) Assignee: Girindus America, Inc., Cincinnati, OH (US)

( * ) Notice: Subject to any disclaimer, the term of this patent is extended or adjusted under 35 U.S.C. 154(b) by 0 days.

(21) Appl. No.: 13/805,614

(22) PCT Filed: Jun. 30, 2011

(86) PCT No.: PCT/EP2011/061057
§ 371 (c)(1),
(2), (4) Date: Dec. 19, 2012

(87) PCT Pub. No.: WO2012/001126
PCT Pub. Date: Jan. 5, 2012

(65) Prior Publication Data
US 2013/0096291 A1  Apr. 18, 2013

Related U.S. Application Data

(60) Provisional application No. 61/360,324, filed on Jun. 30, 2010.

(51) Int. Cl.
*C07H 21/00* (2006.01)
(52) U.S. Cl.
USPC ......................... 536/25.3; 536/18.5; 536/18.6
(58) Field of Classification Search
None
See application file for complete search history.

(56) References Cited

U.S. PATENT DOCUMENTS

| | | | |
|---|---|---|---|
| 3,678,017 | A | 7/1972 | Shelton et al. |
| 3,904,664 | A | 9/1975 | Shelton et al. |
| 3,915,940 | A | 10/1975 | Vander Kooi |
| 6,506,894 | B1 | 1/2003 | Reese et al. |
| 7,019,127 | B2 | 3/2006 | Reese et al. |
| 7,723,528 | B2 | 5/2010 | Guzaev |

FOREIGN PATENT DOCUMENTS

| | | |
|---|---|---|
| CA | 1229345 A1 | 11/1987 |
| GB | 1374298 A | 11/1974 |
| WO | WO 9808809 A1 | 3/1998 |
| WO | WO 9849181 A1 | 11/1998 |
| WO | WO 2010072831 A1 | 7/2010 |

OTHER PUBLICATIONS

U.S. Appl. No. 13/165,918, filed Jun. 22, 2011, Adam Wieslaw Mazur, et al.
Hopper, R. J., "New Types of Premature Vulcanization Inhibitors", 1974, Rubber Chemistry and Technology, vol. 47, Issue No. 1, pp. 79-87; 9 pgs.
Dreef, C.E., et al—"A Convenient Approach Towards the Conversion of H-Phosphonate and H-Phosphonothioate Diesters into Phosphoro(di)thioate Derivatives", 1990, Synlett, Georg Thiem Verlag pp. 481-483; 3 pgs.
Nielsen, Peter E., "Methods in Molecular Biology, vol. 208: Peptic Nucleic Acids: Methods and Protocols", 2002, P.E. Nielsen and Humana Press Inc., Editors, Totowa, NJ, pp. 3-26; 24 pgs.
Peterson, Michael, et al—"LNA: a versatile tool for therapeutics and genomics", 2003, Trends in Biotechnology, vol. 21, Issue No. 2, pp. 74-81; 8 pgs.
Eckstein, Fritz—"Review—Phosphorothioate Oligodeoxynucleotides: What Is Their Origin and What Is Unique About Them?", 2000, Antisense and Nucleic Acid Drug Development, vol. 10, Issue No. 2, pp. 117-121; 5 pgs.
Thiviyanathan Varatharasa, et al—"Structure of Hybrid Backbone Methylphosphonate DNA Heteroduplexes: Effect of R and S Stereochemistry", 2002, Biochemistry, vol. 41, Issue No. 3, pp. 827-838; 12 pgs.
Gryaznov, Sergei M.—"Oligonucleotide N3'→P5' phosphoramidates as potential therapeutic agents", 1999, Biochimica et Biophysica Acta.1489, vol. 10, Issue No. 1, pp. 131-140; 10 pgs.
Pruzan, Ronald, etal—"Allosteric inhibitors of telomerase: oligonucleotide N3'→P5' phosphoramidates", 2002, Nucleic Acids Research, vol. 30, Issue No. 2, pp. 559-568; 10 pgs.
Gryaznov, Sergei M. , et al—"Telomerase Inhibitors—Oligonucleotide Phosphoramidates As Potential Therapeutic Agents", 2001, Nucleosides, Nucleotides & Nucleic Acids, vol. 20, Issue Nos. 4-7; pp. 401-410; 10 pgs.
Shea-Herbert, Brittney, et al—"Oligonucleotide N3'→P5' phosphoramidates as efficient telomerase inhibitors", 2002, Oncogene, vol. 21, Issue No. 4, pp. 638-642; 5 pgs.

*Primary Examiner* — Patrick Lewis

(57) ABSTRACT

A method for synthesizing an oligonucleotide which comprises using a sulfurizing agent of general formula (I) for sulfurizing at least one phosphorus internucleotide linkage of a precursor of the oligonucleotide, wherein R is an aryl group or a heteroaryl group, which is bonded to the S-atom through an annular carbon atom; and $R_1$ and $R_2$ are independently organic residues, preferably a C1-C20 hydrocarbon residue. The method may further comprise purifying the oligonucleotide. Also included is a process for the synthesis of the sulfurizing agent.

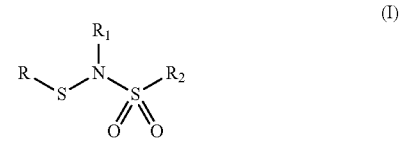

(I)

25 Claims, No Drawings

METHOD OF USING N-THIO COMPOUNDS FOR OLIGONUCLEOTIDE SYNTHESIS

CROSS-REFERENCE TO RELATED APPLICATIONS

The present invention application is a U.S. national stage entry under 35 U.S.C. §371 of International Application No. PCT/EP2011/061057 filed Jun. 30, 2011, which claims priority to U.S. provisional patent application No. 61/360,324 filed Jun. 30, 2010, the whole content of which is incorporated by reference for all purposes.

TECHNICAL FIELD

The present invention relates to the preparation of oligonucleotides by using novel sulfurizing reagents.

BACKGROUND ART

Oligonucleotides belong to a class of biopharmaceuticals with a great potential for therapies of various diseases including cancer, viral infections and inflammatory disease to name a few. An important approach to advancing oligonucleotides as therapeutics involve modifications of the oligomer backbone to provide, among other things, metabolic resistance, chemical stability and to improve in vivo transport to the site of action. Examples of modified backbone chemistries include: peptide nucleic acids (PNAs) (see Nielsen, Methods Mol. Biol., 208:3-26, 2002), locked nucleic acids (LNAs) (see Petersen & Wengel, Trends Biotechnol., 21(2):74-81, 2003), phosphorothioates (see Eckstein, Antisense Nucleic Acid Drug Dev., 10(2):117-21, 2000), methylphosphonates (see Thiviyanathan et al., Biochemistry, 41(3):827-38, 2002), phosphoramidates (see Gryaznov, Biochem. Biophys. Acta, 1489(1):131-40, 1999; Pruzan et al., Nucleic Acids Res., 30(2):559-68, 2002), thiophosphoramidates (see Gryaznov et al., Nucleosides Nucleotides Nucleic Acids, 20(4-7):401-10, 2001; Herbert et al., Oncogene, 21(4):638-42, 2002).

In contrast to large selection of reagents available for introducing the unsubstituted sulfur atom to phosphorus esters, the spectrum of groups allowing for sulfurization of H-phosphonate esters with the protected sulfur is limited (e.g. Dreef, et al. Synlett, 481-483, 1990, U.S. Pat. No. 6,506,894). Practically, only the cyanoethylsulfide group has been used extensively in this reaction during the solution synthesis of oligonucleotides with chromatographic purification at each step. Patent Application PCT/EP2009/067902 in the name of the applicant the contents of which is incorporated by reference into the present patent application discloses novel sulfurizing reagents, a process for their manufacture and their use in the economical and convenient synthesis and purification of phosphorothioate oligonucleotides in solution via the H-phosphonate method. A critical problem in the solution synthesis of oligonucleotides concerns the necessity to obtain high substrate conversions with excellent specificity at each synthetic step giving high purity products in a form that facilitates simple purification, in particular avoiding chromatography. Given the lack of methods allowing for economical solution phase synthesis, the solution phase technology does not seem to be currently used for commercial scale oligonucleotide synthesis.

The invention makes now available a new method for the synthesis of oligonucleotides by using novel sulfurizing reagents, which allows for an economical and efficient synthesis and purification of oligonucleotides notably in solution.

DISCLOSURE OF INVENTION

The present invention relates in particular to a method for synthesizing an oligonucleotide which comprises using a sulfurizing agent of general formula (I):

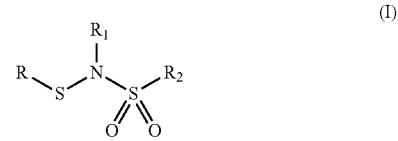

wherein
R is selected from a group consisting of an aryl group and a heteroaryl group which is bonded to the S-atom through an annular carbon atom.
$R_1$ and $R_2$ are independently organic residues, preferably a C1-C20, optionally unsaturated or aromatic, hydrocarbon residue;
for sulfurizing at least one phosphorus internucleotide linkage of a precursor of said oligonucleotide.

The invention has a number of advantages over existing methods of P—S linkage formation, in particular in the synthesis of oligonucleotides carried out preferably via the H-phosphonate method. For example, the residue R transferred e.g. to an oligonucleotide with the novel reagent can facilitate crystallization or precipitation of oligonucleotides, allowing for simple purification of the products with minimum or no chromatography. An important factor in developing an economical process for the synthesis of oligonucleotides, especially in solution, is the purity of the transformation product at each step of oligonucleotide chain elongation. Even though the process according to the invention secures high yields and purity of the products, each elongation cycle comprises generally three steps and it is advantageous to remove even small amounts of impurities which would otherwise accumulate along the way. Because of large number of steps, the use of chromatography at each step may not be economically feasible in the practical large scale oligonucleotide synthesis.

The term "oligonucleotide", in the frame of the present invention, denotes in particular an oligomer of nucleoside monomeric units comprising sugar units connected to nucleobases, said nucleoside monomeric units being connected by internucleotide bonds. An "internucleotide bond" refers in particular to a chemical linkage between two nucleoside moieties, such as the phosphodiester linkage typically present in nucleic acids found in nature, or other linkages typically present in synthetic nucleic acids and nucleic acid analogues. Such internucleotide bond may for example include a phospho or phosphite group, and may include linkages where one or more oxygen atoms of the phospho or phosphite group are either modified with a substituent or replaced with another atom, e.g., a sulfur atom, or the nitrogen atom of a mono- or di-alkyl amino group. Typical internucleotide bonds are diesters of phosphoric acid or its derivatives, for example phosphates, thiophosphates, dithiophosphate, phosphoramidates, thio phosphoramidates.

The term "nucleoside" is understood to denote in particular a compound consisting of a nucleobase connected to a sugar. Sugars include, but are not limited to, furanose ring such as ribose, 2'-deoxyribose and non-furanose ring such as cyclohexenyl, anhydrohexitol, morpholino. The modifications, substitutions and positions indicated hereinafter of the sugar included in the nucleoside are discussed with reference to a furanose ring, but the same modifications and positions also apply to analogous positions of other sugar rings. The sugar may be additionally modified. As non limitative examples of the modifications of the sugar mention can be notably made of modifications at e.g. the 2'- or 3'-position, in particular 2'-position of a furanosyl sugar ring including for instance hydrogen; hydroxy; alkoxy such as methoxy, ethoxy, allyloxy, isopropoxy, butoxy, isobutoxy, methoxyethyl, alkoxy, phenoxy; azido; amino; alkylamino; fluoro; chloro and bromo; 2'-4'- and 3'-4'-linked furanosyl sugar ring modifications, modifications in the furanosyl sugar ring including for instance substitutions for ring 4'-O by S, $CH_2$, NR, CHF or $CF_2$.

The term "nucleobase" is understood to denote in particular a nitrogen-containing heterocyclic moiety capable of pairing with a, in particular complementary, nucleobase or nucleobase analog. Typical nucleobases are the naturally occurring nucleobases including the purine bases adenine (A) and guanine (G), and the pyrimidine bases thymine (T), cytosine (C) and uracil (U), and modified nucleobases including other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine, 3-deazaguanine and 3-deazaadenine, and fluorinated bases. Further modified nucleobases include tricyclic pyrimidines such as phenoxazine cytidine (1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Other potentially suitable bases include universal bases, hydrophobic bases, promiscuous bases and size-expanded bases.

"Oligonucleotide" typically refers to a nucleoside subunit polymer having from about 2 to about 50 contiguous subunits. The nucleoside subunits can be joined by a variety of intersubunit linkages. Further, "oligonucleotides" includes modifications, known to one skilled in the art, to the sugar backbone (e.g., phosphoramidate, phosphorodithioate), the sugar (e.g., 2' substitutions such as 2'-F, 2'-OMe), the base, and the 3' and 5' termini. Typically, in this invention the oligonucleotide comprises from 2 to 30 nucleotides. Preferably, it comprises from 3 to 30 nucleotides. In different embodiments of this invention, the oligonucleotide contains nucleosides selected from ribonucleosides, 2'-deoxyribonucleosides, 2'-substituted ribonucleosides, 2'-4'-locked-ribonucleosides, 3'-amino-ribonucleosides, 3'-amino-2'-deoxyribonucleosides.

The term "aryl group" is intended to denote in particular an aromatic carbocyclic system comprising from 6 to 24 carbon atoms, preferably from 6 to 12 carbon atoms. The aryl group may be unsubstituted or substituted for example, with aryl or heteroaryl, alkyl groups, cycloalkyl, or functional groups. Preferably, the aryl group is substituted in position 4 with alkyl or halogens.

The term "heteroaryl" is intended to denote in particular an aromatic carbocyclic system comprising from 5 to 24 atoms, preferably from 5 to 12 atoms, at least one of which is a hetero atom. The hetero atom is often chosen from B, N, O, Si, P and S. It is more often chosen from N, O and S.

The term "alkyl group" is intended to denote in particular a linear or branched alkyl substituent comprising from 1 to 20 carbon atoms, preferably 1, 2, 3, 4, 5, 6, 7, 8, 9 or 10 carbon atoms. Specific examples of such substituents are methyl, ethyl, n-propyl, isopropyl, n-butyl, isobutyl, tert-butyl, n-pentyl, isopentyl, n-hexyl, 2-hexyl, n-heptyl, n-octyl and benzyl.

The term "cycloalkyl group" is intended to denote in particular a substituent comprising at least one saturated carbocycle containing 3 to 10 carbon atoms, preferably 5, 6 or 7 carbon atoms. Specific examples of such substituents are cyclopropyl, cyclobutyl, cyclopentyl, cyclohexyl and cycloheptyl.

The term "functional group" is intended to denote in particular a substituent comprising or consisting of a hetero atom. The hetero atom is often chosen from B, N, O, Al, Si, P, S, Sn, As and Se and the halogens. It is more often chosen from N, O, S and halogen, in particular halogen.

The functional group generally comprises 1, 2, 3, 4, 5 or 6 atoms.

By way of functional groups, mention may, for example, be made of halogens, a hydroxyl group, an alkoxy group, a mercapto group, an amino group, a nitro group, a carbonyl group, an acyl group, an optionally esterified carboxyl group, a carboxamide group, a urea group, a urethane group and the thiol derivatives of the abovementioned groups containing a carbonyl group, phosphine, phosphonate or phosphate groups, a sulphoxide group, a sulphone group and a sulphonate group.

The term "organic residue" is intended to denote in particular linear or branched alkyl or alkylene groups which may contain hetero atoms, such as in particular boron, silicon, nitrogen, oxygen or sulphur atoms and halogen atoms, cycloalkyl groups, heterocycles and aromatic systems. The organic residue may contain double or triple bonds and functional groups.

The organic residue comprises at least 1 carbon atom. It often comprises at least 2 carbon atoms. It preferably comprises at least 3 carbon atoms. More particularly preferably, it comprises at least 5 carbon atoms.

The organic residue generally comprises at most 100 carbon atoms. It often comprises at most 50 carbon atoms. It preferably comprises at most 40 carbon atoms. More particularly preferably, it comprises at most 30 carbon atoms.

The term "alkylene group" or "cycloalkylene group" is intended to denote in particular the divalent radicals derived from the alkyl or cycloalkyl groups as defined above.

When the organic residue contains one or optionally more double bonds, it is often chosen from an alkenyl or cycloalkenyl group comprising from 2 to 20 carbon atoms, preferably 2, 3, 4, 5, 6, 7, 8, 9 or 10 carbon atoms. Specific examples of such groups are vinyl, 1-allyl, 2-allyl, n-but-2-enyl, isobutenyl, 1,3-butadienyl, cyclopentenyl, cyclohexenyl and styryl.

When the organic residue contains one or optionally more triple bonds, it is often chosen from an alkinyl group comprising from 2 to 20 carbon atoms, preferably 2, 3, 4, 5, 6, 7, 8, 9 or 10 carbon atoms. Specific examples of such groups are ethinyl, 1-propinyl, 2-propinyl, n-but-2-inyl and 2-phenylethinyl.

When the organic residue contains one or optionally more aromatic systems, it is often an aryl or an alkylaryl group comprising from 6 to 24 carbon atoms, preferably from 6 to 12 carbon atoms. Specific examples of such groups are phenyl, 1-tolyl, 2-tolyl, 3-tolyl, xylyl, 1-naphthyl and 2-naphthyl.

The term "heterocycle" is intended to denote in particular a cyclic system comprising at least one saturated or unsaturated ring made up of 3, 4, 5, 6, 7 or 8 atoms, at least one of which is a hetero atom. The hetero atom is often chosen from B, N, O, Si, P and S. It is more often chosen from N, O and S.

Specific examples of such heterocycles are aziridine, azetidine, pyrrolidine, piperidine, morpholine, 1,2,3,4-tetrahydroquinoline, 1,2,3,4-tetrahydroisoquinoline, perhydroquinoline, perhydroisoquinoline, isoxazolidine, pyrazoline, imidazoline, thiazoline, tetrahydrofuran, tetrahydrothiophene, pyran, tetrahydropyran and dioxane.

The organic residues as defined above may be unsubstituted or substituted with functional groups. It is understood that same definition for the functional groups given herein before equally applies.

In a preferred embodiment of the process according to the invention, R is an unsubstituted or substituted phenyl group, preferably, R is halophenyl or alkylphenyl. R is in particular a 4-halophenyl group or a 4-alkylphenyl group, commonly a 4-($C_1$-$C_4$-alkyl)phenyl group; R is more preferably a 4-haloalkyl group, and is especially a 4-chlorophenyl group; and $R_1$ and $R_2$ are independently a C1-C20, saturated, unsaturated, heterocyclic or aromatic, hydrocarbon residue.

As mentioned above, $R_1$ and $R_2$ can be the same or different.

When $R_1$ is a saturated hydrocarbon residue, it is preferably selected from linear, branched or cyclic alkyl residues. $R_1$ can for example be independently selected from lower alkyl or cycloalkyl (C1-C7) residues. Particular saturated hydrocarbon residues are selected from methyl, ethyl, n-propyl, isopropyl, n-butyl, sec-butyl, tert. butyl, cyclopentyl and cyclohexyl. A methyl, ethyl or n-propyl group is preferred. A methyl group is more particularly preferred. When $R_1$ is an aromatic residue, it is suitably selected from aromatic systems having from 5 to 14 atoms. Particular aromatic residues are selected from phenyl and naphthyl groups which phenyl groups can be substituted, for example, by aryl or heteroaryl, alkyl, cycloalkyl, heterocycle or heterosubstitutents such as halogens, amines, ethers, carboxylates, nitro, thiols, sulfonic and sulfones. Also the naphthyl groups can be substituted, for example, by aryl or heteroaryl, alkyl, cycloalkyl, heterocycle or heterosubstitutents such as halogens, amines, ethers, carboxylates, nitro, thiols, sulfonic and sulfones. If $R_1$ is an aromatic residue, a phenyl group is preferred.

When $R_1$ is a heterocyclic residue, it is often selected from heterocycles containing at least one annular N, O or S atom which are bonded to N through an annular carbon atom. Particular examples of such heterocyclic residues include pyridine and furan.

When $R_2$ is a saturated hydrocarbon residue, it is preferably selected from linear, branched or cyclic alkyl residues. $R_2$ can for example be independently selected from lower alkyl or cycloalkyl (C1-C7) residues. Particular saturated hydrocarbon residues are selected from methyl, ethyl, n-propyl, isopropyl, n-butyl, sec-butyl, tert. butyl, cyclopentyl and cyclohexyl. A methyl, ethyl or n-propyl group is preferred. A methyl group is more particularly preferred. When $R_2$ is an aromatic residue, it is suitably selected from aromatic systems having from 5 to 14 atoms. Particular aromatic residues are selected from phenyl and naphthyl groups which phenyl and naphthyl groups can be substituted, for example, by aryl or heteroaryl, alkyl, cycloalkyl, heterocycle or heterosubstitutents such as halogens, amines, ethers, carboxylates, nitro, thiols, sulfonic and sulfones. If $R_2$ is an aromatic residue, a phenyl group is preferred.

In a preferred embodiment, $R_1$ and $R_2$ are identical and denote methyl.

When $R_2$ is a heterocyclic residue, it is often selected from heterocycles containing at least one annular N, O or S atom which are bonded to the sulfonyl group (S(O)$_2$) through an annular carbon atom. Particular examples of such heterocyclic residues include pyridine and furan.

In a particular aspect, $R_2$ corresponds to formula (II)

wherein $R_x$ and $R_y$ are independently selected from alkyl or (hetero)aryl. Preferably $R_x$ and/or $R_y$ are alkyl groups. In this case $R_x$ and/or $R_y$ can for example be selected from lower alkyl or cycloalkyl (C1-C7) residues. Particular alkyl groups are selected from methyl, ethyl, n-propyl, isopropyl, n-butyl, sec-butyl, tert butyl, cyclopentyl and cyclohexyl. A methyl, ethyl or n-propyl group is preferred. In a particular preferred aspect, $R_x$ and $R_y$ are both alkyl groups, in particular as described herein before. A N,N-dimethyl or N,N-diethyl group is more particularly preferred. In another aspect of this embodiment $R_x$ and $R_y$ form together a 3 to 8 membered ring optionally containing an additional annular heteroatom selected from O, N and S. Particular examples include a N-piperidyl or an N-pyrrolidyl group.

It is also understood that the mentioned substituents may be optionally substituted, for example by halogen or alkoxy substituents or they may be modified, for example by inclusion of catenary heteroatoms, in particular oxygen into an alkyl chain.

It has been found that the sulfurization agent according to the invention allows for particularly efficient sulfur transfer, in particular to form S-protected phosphorthioate internucleotide linkages of formula P—S—R wherein R is as described above in oligonucleotides. The sulfurizing agent according to the invention introduces a protected sulfur from which the protective group can be cleaved selectively and efficiently.

In the method according to the invention, the molar ratio of sulfurizing agent relative to the amount of phosphorus internucleotide linkages to be sulfurized is generally at least 1.0, often from 1.0 to 4.0, more often from 1.0 to 2.0, preferably from 1.05 to 2.0.

A particular aspect of this invention relates to a method for synthesizing an oligonucleotide which comprises using a solution of a sulfurizing agent of general formula (I):

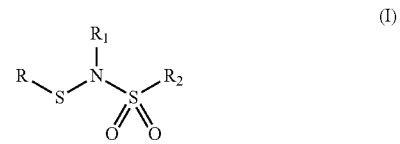

wherein
R is selected from a group consisting of an aryl group and a heteroaryl group; which is bonded to the S-atom through an annular carbon atom.
$R_1$ and $R_2$ are independently organic residues, preferably a C1-C20, optionally unsaturated or aromatic, hydrocarbon residue;

for sulfurizing at least one phosphorus internucleotide linkage of a precursor of said oligonucleotide.

The definitions and preferences described above for the sulfurizing agent used in the method according to the invention equally apply when the sulfurizing agent is in solution.

For the purpose of the present invention, the term "solution" is intended to denote a homogeneous mixture composed of one or more substances, known as solutes, in particular the sulfurizing agent dissolved in another substance, known as a solvent.

For the purpose of the present invention, a homogeneous mixture is a mixture of two or more compounds that are visually indistinguishable from each other.

For the purpose of the present invention, "a solution of a sulfurizing agent" is understood to denote in particular a solution of the sulfurizing agent in a solvent selected from an organic solvent ("organic solution") or mixtures thereof.

The organic solvent to be used may, for example, be selected from nitrogen containing solvents such as amide solvents including for example N,N-dimethylacetamide (DMA), N,N-dimethylformamide (DMF), N-methylpyrrolidone (NMP), dimethylsulfoxide (DMSO); N-heterocyclic solvents including for example pyridine; nitrile solvents including for example acetonitrile; aromatic hydrocarbon type solvents such as benzene, toluene; halogenated hydrocarbon type solvents such as chlorinated hydrocarbon solvents including for example dichloromethane (DCM) and chloroform, esters such as ethyl acetate (AcOEt) and isopropyl acetate (AcOiPr) and ethers such as diethyl ether, diisopropyl ether, dioxane, tetrahydrofuran (THF) and MTBE. Preferably, the organic solvent is selected from halogenated hydrocarbon solvents, pyridine and acetonitrile. Preferably, the sulfurizing agent is dissolved in a halogenated hydrocarbon solvent. More preferably, the organic solvent is selected from chlorinated hydrocarbon type solvents. Good results are obtained with dichloromethane.

It has been found surprisingly that the sulfurizing agent can be efficiently dissolved in the organic solvent providing hereby a concentrated organic solution. Consequently, a lower consumption of the organic solvent makes advantageously the method of the present invention more economical and environmentally friendlier and safer.

In the method according to the invention, the sulfurizing agent content in the solution is generally equal to or at least 1% wt relative to the total weight of sulfurizing agent and organic solvent. In preferred embodiments, the sulfurizing agent content is equal to or at least 1% wt relative to the total weight of sulfurizing agent and aprotic polar organic solvent. In some embodiments, the sulfurizing agent content in the solution is greater than 1% wt relative to the total weight of sulfurizing agent and organic solvent which preferably is an aprotic polar organic solvent. The sulfurizing agent content is often greater than or equal to 20% wt. Preferably, the sulfurizing agent content is greater than or equal to 40% wt. The sulfurizing agent content in the solution is generally at most 60% wt relative to the total weight of sulfurizing agent and organic solvent which preferably is an aprotic polar organic solvent. In a specific preferred embodiment, the sulfurizing agent used in the method according to the invention is dissolved in a halogenated hydrocarbon solvent, in particular a chlorinated hydrocarbon solvent such as methylene chloride and the sulfurizing agent content in the halogenated hydrocarbon solvent is as described here before.

In the method according to the invention, the phosphorus internucleotide linkage of the precursor is formed by a coupling reaction between two reactants selected from nucleotides and oligonucleotides. Information concerning such coupling reaction can be found for example in the Patent Application PCT/EP2009/067902 and illustrated in the example below.

The invention thus relates in another specific aspect to a method for synthesizing an oligonucleotide comprising the following steps:
(a) a coupling step wherein a phosphorus internucleotide linkage of the precursor is formed between two reactants selected from nucleotides and oligonucleotides, and
(b) a sulfurization step wherein the sulfurizing agent of formula (I), as described above, is used to sulfurize said phosphorus internucleotide linkage.

In a most preferred aspect of the invention described herein, the phosphorus internucleotide linkage is an H-phosphonate diester bond.

Step (a) of said synthesis method preferably comprises forming the H-phosphonate diester bond by coupling an H-phosphonate monoester salt with a protected nucleoside or oligonucleotide having a free hydroxy group. The coupling is preferably carried out in solution phase.

Step (a) is preferably carried out in an aprotic polar organic solvent for example a halogenated solvent or nitrogen containing solvents, more particularly N-heterocyclic solvents or chlorinated hydrocarbon, even more particularly acetonitrile and pyridine and preferably pyridine. The reaction to form an H-phosphonate diester is preferably activated by a carboxylic acid halide, in particular pivaloyl chloride.

Step (a) is generally carried out at a temperature from −40° C. to 30° C., preferably from 0° C. to 20° C.

In step (a) the process according to the invention and in the particular embodiments thereof, the liquid reaction medium generally contains at least 10% by weight of H-phosphonate oligonucleotide relative to the total weight of the reaction medium. Preferably, this content is at least 20% weight. The liquid reaction medium generally contains at most 50% by weight of H-phosphonate oligonucleotide relative to the total weight of the reaction medium.

The coupling product of step (a), in particular an H-phosphonate, may be isolated and subsequently sulfurized in step (b). It may also, preferably, be used without isolation in step (b). Sulfurization of formed diester can be carried by in-situ addition of the sulfurizing reagent, suitably dissolved in an appropriate solvent, as described above or after pre-purifying formed diester from the reaction mixture.

Step (b) is preferably carried out in an aprotic polar organic solvent such as for example a solvent comprising a halogenated hydrocarbon solvent, in particular a chlorinated hydrocarbon solvent such as methylene chloride. In a particular aspect, step (b) is carried out in a solvent mixture comprising a halogenated hydrocarbon solvent and nitrogen containing solvents, more particularly N-heterocyclic solvents, preferably pyridine. A pyridine/methylene chloride mixture is more particularly preferred, in particular when the coupling product of step (a) is sulfurized without isolation.

Step (b) is generally carried out at a temperature of from −40° C. to 30° C., preferably from 0° C. to 20° C.

In step (b), the molar ratio of sulfurizing agent relative to the amount of internucleotide linkages to be sulfurized is generally at least 1, often from 1.5 to 4.0, preferably from 2.0 to 3.0.

In one embodiment, in step (b), the molar ratio of sulfurizing agent relative to the amount of phosphorous internucleotide linkages to be sulfurized is generally at least 1, often from 1.0 to 4.0, preferably from 1.0 to 2.0, very preferably from 1.05 to 2.

Very satisfactory results may also be obtained when said molar ratio of sulfurizing agent to the amount of internucleotide linkages, and phosphorus internucleotide linkages, respectively, is in a preferred range of from 1.0 to 2.0.

In step (b) the intermediate H-phosphonate diester is preferably activated by an activator, in particular a base. Suitable bases include alkylamines, in particular tertiary alkylamines, diisopropylethylamine is preferred. A second particular object of the invention relates to a process for the synthesis of the sulfurizing agent, as described above, which comprises (a) reacting a sulfuryl halide, preferably sulfuryl chloride with a thiol of formula R—S—H wherein R is aromatic selected from the group consisting of aryl, alkylaryl, haloaryl, nitroaryl, alkoxyaryl to produce an intermediate product of formula R—S—W, wherein R is described as above and W is halogen, preferably Cl and, (b) reacting said intermediate product with an N-sulfonyl compound of formula $R_1$—NH—$S(O)_2$—$R_2$, wherein $R_1$ and $R_2$ are independently organic residues, preferably a C1-C20, optionally unsaturated or aromatic, hydrocarbon residue.

The sulfurizing agent may be used in the method for synthesizing the oligonucleotide as described above. The definitions and preferences described above for the method according to the invention equally apply to the process according to the invention. In particular, R is preferably halophenyl, more preferably, a 4-halophenyl, and especially 4-chlorophenyl. $R_1$ and $R_2$ are preferably selected from lower alkyl or cycloalkyl (C1-C7), phenyl including substituted phenyl and naphthyl groups, more preferably a methyl group. Also the naphthyl groups may be substituted. The preferred optional substituents of the phenyl and naphthyl groups are given above. Most preferably, $R_1$ and $R_2$ are methyl.

In the process according to the invention for the synthesis of a sulfurizing agent, the reaction of step (a) is generally carried out in an aprotic organic solvent such as for example a halogenated solvent, in particular a chlorinated solvent such as carbon tetrachloride.

In the process according to the invention for the synthesis of a sulfurizing agent, the reaction of step (a) is generally carried out at a temperature of from –80° C. to 30° C.

In the process according to the invention for the synthesis of a sulfurizing agent, the reaction of step (b) is generally carried out in an aprotic polar organic solvent such as for example a halogenated hydrocarbon solvent, in particular a chlorinated hydrocarbon solvent such as methylene chloride.

In the process according to the invention for the synthesis of a sulfurizing agent, the reaction of step (b) is generally carried out at a temperature of from –20° C. to 50° C., preferably from 0° C. to 30° C.

In a third aspect, the invention relates to a method for purifying an oligonucleotide obtained in accordance with the method of the invention as described herein before. In one embodiment of this aspect, the method comprises precipitating the oligonucleotide. In more specific embodiments, this method further comprises extraction of the oligonucleotide, in particular from solid material recovered from the precipitation step, with a solvent. Suitable solvents for extraction include a polar organic solvent.

It has been found that the purification can be effectively accomplished by a combination of precipitation and extraction techniques of the protected oligonucleotide obtained according to the described method. The exact conditions of precipitation can be determined on account of given sequence and length of the oligonucleotide. The precipitation method generally comprises (a) dissolving the oligonucleotide in a polar organic solvent and (b) adding a non-polar organic solvent until the solution becomes turbid.

It has been found that the oligonucleotides according to the invention can generally be isolated and purified by precipitation.

The solvent used to dissolve the oligonucleotide in step (a) is preferably selected from halogenated hydrocarbons such as methylene chloride and chloroform, nitrogen containing solvents such as acetonitrile and pyridine, and carbonyl-containing solvents such as acetone.

Generally, in step (a), a solvent volume is used ranging from about 0.5 (n+1) mL to about 2.0 (n+1) mL, preferably, about 1.0 (n+1) mL, where n is the millimoles number of phosphorothioate triester linkages.

The solution of the oligonucleotide is treated with a non-polar organic solvent preferably selected from hydrocarbons, for example alkane solvents such as hexane, an ether solvent or ether solvents in particular MTBE and their mixtures, such as, preferably hexane/MTBE mixtures until the solution becomes turbid. In another particular embodiment the turbid solution is subsequently treated with a precipitation aid.

In this case the precipitation aid is generally selected from inert porous solids preferably selected from Celite, charcoal, wood cellulose and chromatography stationary phases such as silica or alumina. Celite is also known as diatomaceous earth.

In this case, the precipitation aid is generally used in an amount ranging from about 0.25 (n+1) g to about 1.5 (n+1) g, preferably, about 0.75 (n+1) g, where n is the millimoles number of phosphorothioate triester linkages.

Preferably, after adding the precipitation aid the mixture is treated with a second fraction of a non-polar organic solvent as described here before. The volume of said fraction generally ranges from about 1 (n+1) mL to about 4 (n+1) mL, preferably, about 2.0 (n+1) mL, wherein n is the millimoles number of phosphorothioate triester linkages.

After precipitation, in particular when a precipitation aid is used, the obtained mixture is generally subjected to a solid/liquid separation operation such as, preferably, a filtration. Preferably, the solid materials obtained in the precipitation step are filtered off and washed. The oligonucleotide is generally recovered from solid recovered from solid/liquid separation operation, in particular from precipitation aid by extraction with a solvent, especially with a polar organic solvent preferably selected from carbonyl-type solvents such as acetone, from nitrogen-containing solvents such as acetonitrile or a formamide type solvent, from polar ethers such as tetrahydrofurane, from halogenated hydrocarbons such as methylene chloride and chloroform or an aliphatic alcohol. The polar organic solvent is preferably selected from acetonitrile, tetrahydrofurane (THF), N,N-dimethylformamide (DMF), and an aliphatic alcohol.

The oligonucleotide obtained from the above precipitation treatment can be further purified by partitioning between an organic solvent and water. This step usually separates polar impurities, which dissolve in the aqueous layer, from the product. In this embodiment, the oligonucleotide is suitably dissolved in a organic solvent, in particular a polar organic solvent in particular selected from acetonitrile, tetrahydrofurane (THF), N,N-dimethylformamide (DMF), and an aliphatic alcohol. In this embodiment, the solvent preferably comprises a mixture of polar organic solvent, preferably selected from acetonitrile, THF, DMF, and an aliphatic alcohol, with an aqueous medium.

The volume of organic solvent used is generally ranging from 2.0 (n+1) mL to 8.0 (n+1) mL, preferably, about 4.0 (n+1) mL, where n is the millimoles number of the phosphorothioate triester linkage. The solution is treated with an aqueous medium, in particular water. The volume of aqueous medium used is generally from about 0.5 volume equivalent of the organic solvent to about 1.5 volume equivalent of the organic solvent, usually about 0.7 volume equivalent of the organic solvent. After treatment with the aqueous medium, an oligonucleotide-containing layer is generally separated and can be further processed, if appropriate, to obtain purified oligonucleotide.

In general, the cleavage of the protecting R group on the phosphorothioate internucleotide linkages can be carried out by oximate treatment. Suitable examples of aldoximes are selected for example from E-2-nitrobenzaldoxime, E-4-nitrobenzaldoxime and syn-pyridine-2-carboxaldoxime. Said cleavage leads in general to phosphodiester internucleotide linkages.

Consequently, the method according to the invention is particularly useful for the manufacture of an oligonucleotide comprising at least one phosphodiester internucleotide linkage.

Should the disclosure of any patents, patent applications, and publications which are incorporated herein by reference conflict with the description of the present application to the extent that it may render a term unclear, the present description shall take precedence.

The following examples are intended to illustrate the invention without, however, limiting its scope

EXAMPLES

In these examples and throughout this specification the abbreviations employed are defined as follows:

$CH_2Cl_2$ is dichloromethane, DIPEA is diisopropylethylamine, MTBE is methyl tert-butyl ether, HCl is hydrochloride acid, $Na_2SO_4$ is sodium sulfate, $N_2$ is nitrogen, $SO_2Cl_2$ is sulfuryl chloride, $NaHCO_3$ is sodium bicarbonate, CDCl3 is deuterated chloroform, THF is tetrahydrofurane, DMSO is dimethylsulfoxide, DMF is N,N-dimethylformamide.

Ap, Gp, Tp are the 2-deoxyribose nucleobases as previous described respectively connected to A, G and T nucleobases as previously described wherein A, G and T are protected as follows:

DMTr is the bis para-methoxy trityl protecting group, known to one skilled in the art, bonded to the 5-O' of the corresponding oligonucleotide as previously described, when linked to it. Lev is the pentan1,4-dione protecting group, known to one skilled in the art, bonded to the 3-O' of the corresponding oligonucleotide as previously described.

Example 1

Synthesis of 4-Chlorophenyl-(N,N-methyl-mesyl)-sulfenamide

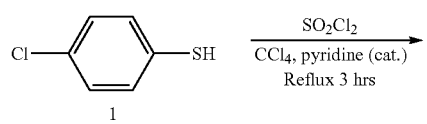

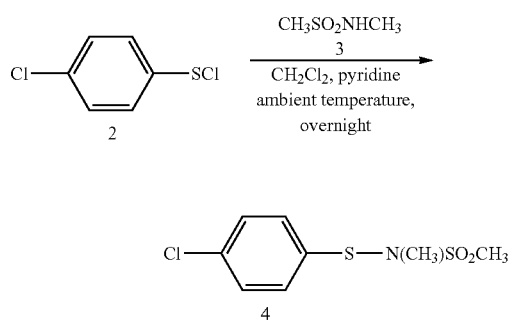

(a) Preparation of 4-chlorobenzene sulfenyl chloride 2

A solution of 4-chlorothiophenol, 1 (20.15 g, 0.139 mol) in 170 mL of anhydrous carbon tetrachloride was placed in a 0.5 L 3-neck round bottom flask equipped with a magnetic stirrer, thermocouple, addition funnel, nitrogen line, heating mantle, condenser and caustic scrubber to absorb acidic gases ($SO_2$ and HCl). A catalytic amount of pyridine (3 mL) was added to the solution, and the flask's content was chilled to ~10° C. Sulfuryl chloride (55.2 g, 0.409 mol) was slowly added to the solution of 1, and the reaction mixture was gently refluxed for 3 hours. The resulting red solution was cooled to room temperature, quickly filtered through glass wool, and concentrated by rotary evaporation to yield 23 g of 4-chlorobenzene sulfenyl chloride, 2 as a viscous red oil. This crude material was used immediately for preparation of 4.

(b) 4-Chlorophenyl-(N,N-methyl-mesyl)-sulfenamide (4)

Crude N-methyl-mesyl amine, 3 (16.6 g, 0.152 mol.) was placed in a 1 L, one-neck round bottom flask and coevaporated with anhydrous acetonitrile (1×150 mL) by rotary evaporation. The residue was dissolved in 120 mL of anhydrous dichloromethane, and anhydrous pyridine (14.5 g, 0.183 mol) and 12 g of molecular sieves were added to this solution. The flask was equipped with a thermocouple, magnetic stirrer, nitrogen line and cooling ice bath. The flask's content was stirred for 10 min, and then chilled to ~0° C.

A solution of crude 4-chlorobenzene sulfenyl chloride, 2 in 80 mL of anhydrous dichloromethane was slowly introduced into a flask containing the amine 3, thereby maintaining the temperature at around 0° C. After completing the addition, the cooling bath was removed, and the resulting cloudy colorless mixture was stirred overnight at ambient temperature.

The reaction was quenched with cold saturated sodium bicarbonate solution (0.4 L), extracted with dichloromethane (2×100 mL) and dried over anhydrous sodium sulfate. After concentration by rotary evaporation, a total of 40 g of dark oil was obtained. This oil was redissolved in a minimum amount of dichloromethane (~20 mL) and filtered via a short (~2 cm) silica gel pad The pad was washed with a mixture of MTBE-hexane=1:1 (~1 L). After concentration of the filtrates, an off-white semi-solid was obtained. A mixture of MTBE-hexane=1:2 (~0.5 L) was added to the residue, and the resulting suspension was chilled on ice. The precipitate was filtered, first washed with a cold mixture of MTBE and hexane (1:2; 50 mL) and then washed with hexane (100 mL), followed by drying until a constant weight was obtained. The desired compound 4 was obtained as a white crystalline solid in 75% yield (24.24 g).

$^1$H NMR (CDCl$_3$, δ): 7.38 (m, 4H), 3.32 (s, 3H), 3.00 (s, 3H)

$^{13}$C NMR APT (CDCl$_3$, δ): 134.64 (up), 134.32 (up), 129.45 (down), 128.63 (down), 42.02 (down), 37.91 (down).

Example 2

Preparation of DMTrO-Tp(s)T-Lev Using Different Sulfurizing Agents

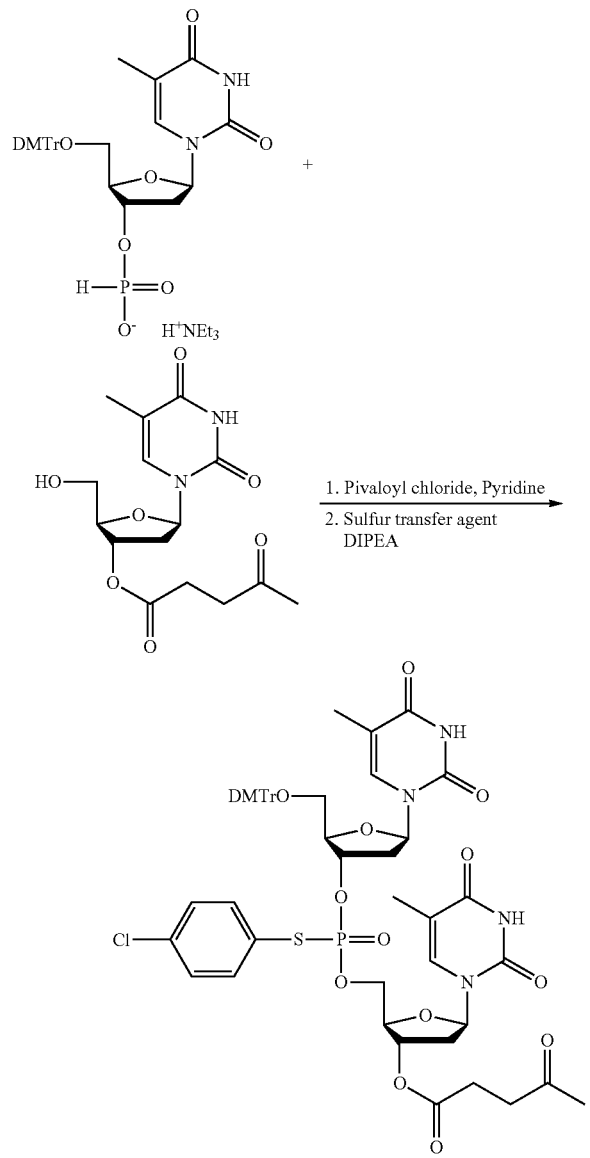

A solution of triethylammonium 5'-O-(4,4'-dimethoxytrityl)-thymidine-3'-H-phosphonate (4.26 g, 6.0 mmol) and 3'-O-levulinylthymidine (1.70 g, 5.0 mmol) in 60 mL of pyridine was evaporated to dryness. To the residue, anhydrous pyridine (12.5 mL) was added and the resulting solution was stirred under argon at 0° C. Pivaloyl chloride (1.24 mL, 10.0 mmol) was slowly added over 3 minutes. The mixture was stirred further at 0° C. for 5 minutes. A solution of 6 mmol of a sulfurizing agent (the respective sulfurizing agents and the amounts used are shown in Table 1) in anhydrous dichloromethane (DCM) or anhydrous pyridine was added, followed by N,N-diisopropylethylamine (0.87 mL, 5.0 mmol) over 2 minutes. The cold bath was removed, and the mixture was stirred at ambient temperature for 30 minutes. The reaction mixture was diluted with 100 mL of dichloromethane and was washed with cold water (100 mL), followed by saturated sodium bicarbonate (100 mL). The organic layer was dried (Na$_2$SO$_4$) and concentrated. The residue was dissolved in 10 mL of dichloromethane and 0.1 mL of triethylamine, and solution A (MTBE:hexane=2:1, 16 mL) was added slowly over 15 minutes under stirring followed by celite (7.5 g). The mixture was stirred and additional solution A (16 mL) was added slowly over 15 minutes. After further stirring for 30 minutes, the mixture was filtered. The solid was washed with a mixture of CH$_2$Cl$_2$/solution A, 1:4 v/v (50 mL×2). The solid was then washed with dichloromethane (50 mL×3). The dichloromethane filtrate was concentrated. The residue was dissolved in 40 mL of acetonitrile and stirred in an ice-water bath, then water (36 mL) was added over 20 minutes. The bottom organic layer was separated and partitioned between dichloromethane (80 mL) and a mixture of saturated sodium bicarbonate (30 mL) and brine (30 mL). The organic layer was dried (Na$_2$SO$_4$) and concentrated to give the desired product as a white solid. $^{31}$P NMR (CDCl$_3$, 121.5 MHz): δ=23.3, 23.2. The results are summarized in Table 1.

TABLE 1

| Sulfurizing agent | Amount of sulfurizing agent equivalent to 6 mmol/ Solution volume of solvent | Yield (%) | HPLC Purity (%) | $^{31}$P NMR Purity (%) |
|---|---|---|---|---|
| Compound 4 | 1.51 g/3 mL anhydrous DCM | 90.0 | 99.3 | 96.1 |
| N-[(4-chlorophenyl)-sulfanyl] succinimide | 1.45 g/6 mL anhydrous DCM | 88.0 | 98.6 | 95.9 |
| N-[(4-chlorophenyl)-sulfanyl] phthalimides | 1.74 g/16 mL anhydrous pyridine | 95.6 | 97.6 | 95.7 |

Example 3

Complete Deprotection of 5'-OH Fully-Protected Trimer as Shown in Scheme Below

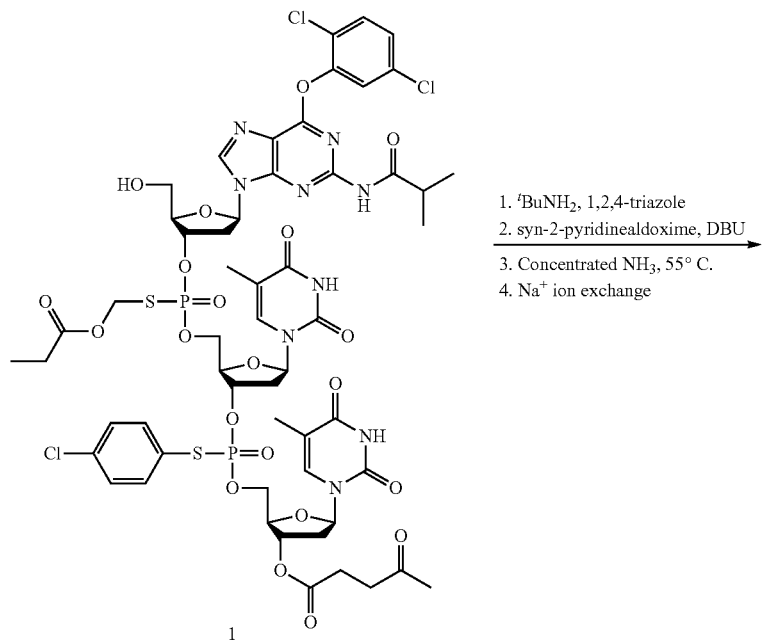

Fully-protected trimer 1 (7.09 g, 5.0 mmol) is rendered anhydrous by evaporation of added pyridine. To the residue, 1,2,4-triazole (690.7 mg, 10.0 mmol), 4 Å molecular sieve (2.0 g) and anhydrous pyridine (25.0 mL) are added. This mixture is stirred and cooled to 0° C. under $N_2$, and tert-butylamine (2.19 g, 30.0 mmol) is added. The resulting mixture then is stirred at room temperature for 4 hours. To the solution, syn-2-pyridinealdoxime (2.44 g, 20.0 mmol) is added, followed by 1,8-diazabicyclo[5.4.0]undec-7-ene (6.09 g, 40.0 mmol). After stirring at room temperature for 15 hours, the molecular sieve is filtered and washed with pyridine (10.0 mL). The filtrate is concentrated. The residue is dissolved in 28% aqueous ammonia (25.0 mL). The resulting solution is heated at 55° C. for 15 hours. After cooling down the mixture is concentrated and purified with a reversal C18 chromatography. The product obtained is applied to a column (100 g) of Amberlite® IR-120 (plus) ion-exchange resin (sodium form). The column is eluted with water, and the desired fractions are combined and lyophilized to give the desired product 2.

The invention claimed is:

1. A method for synthesizing an oligonucleotide which comprises using a sulfurizing agent of general formula (I):

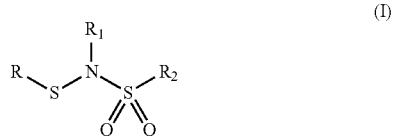

wherein
R is selected from a group consisting of an aryl group and a heteroaryl group; said R being bonded to the S-atom through an annular carbon atom;

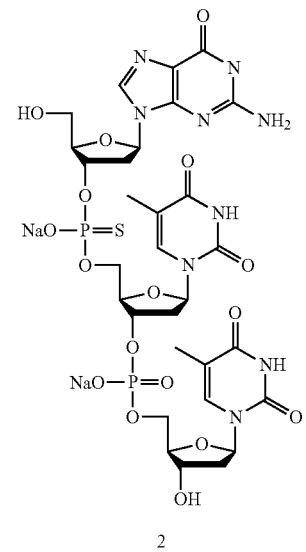

$R_1$ and $R_2$ are independently organic residues;
for sulfurizing at least one phosphorus internucleotide linkage of a precursor of said oligonucleotide.

2. The method according to claim 1, wherein R is a halophenyl or alkylphenyl group.

3. The method according to claims 1, wherein $R_1$ and $R_2$ are selected from the group consisting of lower alkyl or cycloalkyl (C1-C7) groups, phenyl group, substituted phenyl groups, naphthyl group, and substituted naphthyl groups.

4. The method according to claim 1, wherein the sulfurizing agent is dissolved in an organic solvent.

5. The method according to claim 1, wherein the molar ratio of said sulfurizing agent to said at least one phosphorus internucleotide linkage to be sulfurized is from 1.0 to 2.0.

6. The method according to claim 1, wherein the precursor of said oligonucleotide contains nucleosides selected from the group consisting ribonucleosides, 2'-deoxyribonucleosides, 2'-substituted ribonucleosides, 2'-4'-locked-ribonucleosides, 3'-amino-ribonucleosides, and 3'-amino-2'-deoxyribonucleosides.

7. The method according to claim 1, wherein said at least one phosphorus internucleotide linkage is an H-phosphonate diester bond.

8. The method according to claim 7, wherein said H-phosphonate diester bond is formed by a coupling reaction, and wherein said coupling is carried out in solution phase.

9. The method according to claim 1, further comprising a step of purifying the oligonucleotide obtained.

10. The method according to claim 9, wherein said step of purifying the oligonucleotide comprises at least precipitating the oligonucleotide.

11. The method according to claim 10, wherein said step of purifying the oligonucleotide further comprises extracting the oligonucleotide with a solvent.

12. The method according to claim 10, wherein said precipitation step comprises dissolving the oligonucleotide in a polar organic solvent.

13. The method according to claim 12, wherein a volume of said polar organic solvent is used ranging from about 0.5 (n+1) mL to about 2.0 (n+1) mL, and wherein n is the millimoles number of phosphorothioate triester linkages.

14. The method according to claim 12, wherein said precipitation step further comprises treating the resulting solution of the oligonucleotide with a non-polar organic solvent selected from the group consisting of hydrocarbons, ether solvents, and mixtures thereof, until the solution becomes turbid.

15. The method according to claim 14, wherein a volume of said non-polar organic solvent is used ranging from about 1 (n+1) mL to about 4 (n+1) mL, and wherein n is the millimoles number of phosphorothioate triester linkages.

16. The method according to claim 14, wherein the turbid solution is treated with a precipitation aid.

17. The method according to claim 16, where said precipitation aid is an inert porous solid selected from the group consisting of Celite, charcoal, wood cellulose, and chromatography stationary phases.

18. The method according to claim 16, wherein said precipitation aid is used in an amount ranging from about 0.25 (n+1) g, to about 1.5 (n+1) g, and wherein n is the millimoles number of phosphorothioate triester linkages.

19. The method according to claim 16 wherein after adding the precipitation aid, the resulting mixture is treated with a second fraction of a non-polar organic solvent with a volume of said second fraction ranging from about 1 (n+1) mL to about 4 (n+1) mL, and wherein n is the millimoles number of phosphorothioate triester linkages.

20. The method according to claims 16, wherein the solid materials obtained in the precipitation step are filtered off and washed.

21. The method according to claim 10, wherein the oligonucleotide is extracted from the oligonucleotide-containing precipitate with a solvent.

22. The method according to claim 21, wherein the solvent comprises a mixture of a polar organic solvent selected from the group consisting of acetonitrile, tetrahydrofuran (THF), N,N-dimethlformamide (DMF), and an aliphatic alcohol, with an aqueous medium, and wherein a volume of said aqueous medium from about 0.5 to about 1.5 volume equivalent of said polar orgsnic solvent is used.

23. A process for the synthesis of a sulfurizing agent of general formula (I):

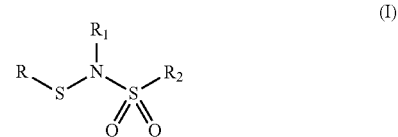

where
R is an aromatic group selected from the group consisting of aryl, alkylaryl, haloarlyl, nitroarly, and alkoxyaryl, R being bonded to the S-atom through an annular carbon atom, and
$R_1$ and $R_2$ are independemtly organic residues,
said process comprising: (a)
reacting a sulfuryl halide with a thiol of formula R—S—H—, to produce an intermediate product of formula R—S—W, wherein R is the same as defined in formula (I), and W is halogen; and, (b) reacting said intermediate product with an N-sulfonyl compound of formula $R_1$—NH—S(O)$_2$—$R_2$, wherein $R_1$ and $R_2$ are the same as defined in formula (I).

24. The process according to claim 23, wherein R is a halophenyl.

25. The process according to claim 23, wherein $R_1$ and $R_2$ are selected from the group consisting of lower alkyl or cycloalkyl (C1-C7) group, phenyl group, substituted phenyl groups, naphthly group, and substituted naphthyl groups.

* * * * *